US009951194B2

(12) United States Patent
Walker et al.

(10) Patent No.: US 9,951,194 B2
(45) Date of Patent: Apr. 24, 2018

(54) IRON OXIDE CONTAINING EFFECT PIGMENTS, THEIR MANUFACTURE AND THEIR USE

(71) Applicant: BASF Corporation, Florham Park, NJ (US)

(72) Inventors: Juergen Walker, Ossining, NY (US);
Gabe Uzunian, Rye, NY (US);
Raimund Schmid, Neustadt (DE);
Aron Wosylus, Bad Durkheim (DE);
Christoph Schwidetzky, Ludwigshafen (DE)

(73) Assignee: BASF CORPORATION, Florham Park, NJ (US)

(*) Notice: Subject to any disclaimer, the term of this patent is extended or adjusted under 35 U.S.C. 154(b) by 0 days.

(21) Appl. No.: 14/044,297

(22) Filed: Oct. 2, 2013

(65) Prior Publication Data
US 2014/0099346 A1 Apr. 10, 2014

Related U.S. Application Data

(60) Provisional application No. 61/710,191, filed on Oct. 5, 2012.

(51) Int. Cl.
C08K 3/00 (2006.01)
A61Q 1/04 (2006.01)
A61Q 1/06 (2006.01)
A61K 8/19 (2006.01)
A61Q 3/02 (2006.01)
A61Q 1/10 (2006.01)
A61Q 3/04 (2006.01)
A61Q 1/02 (2006.01)
A61K 8/96 (2006.01)
A61K 8/02 (2006.01)
C09C 1/00 (2006.01)
C09C 1/24 (2006.01)
A61Q 1/08 (2006.01)

(52) U.S. Cl.
CPC .......... C08K 3/0033 (2013.01); A61K 8/0241 (2013.01); A61K 8/19 (2013.01); A61K 8/965 (2013.01); A61Q 1/02 (2013.01); A61Q 3/04 (2013.01); C09C 1/0015 (2013.01); C09C 1/24 (2013.01); A61K 2800/43 (2013.01); A61K 2800/621 (2013.01); A61Q 1/04 (2013.01); A61Q 1/06 (2013.01); A61Q 1/08 (2013.01); A61Q 1/10 (2013.01); A61Q 3/02 (2013.01); C01P 2006/80 (2013.01)

(58) Field of Classification Search
CPC .......... A61K 2800/43; A61K 2800/621; A61K 8/19; A61Q 1/02; A61Q 1/04; A61Q 1/06; A61Q 1/08; A61Q 1/10; A61Q 3/02; C08K 3/0033

USPC ..... 424/401, 63, 70.7, 61, 64, 646; 106/428; 427/213, 212
See application file for complete search history.

(56) References Cited

U.S. PATENT DOCUMENTS

| 3,926,659 | A | † | 12/1975 | Bernhard et al. |
| 4,328,042 | A | | 5/1982 | Ostertag et al. |
| 4,344,987 | A | † | 8/1982 | Ostertag |
| 4,552,593 | A | | 11/1985 | Ostertag |
| 4,867,793 | A | † | 9/1989 | Franz |
| 4,978,394 | A | | 12/1990 | Ostertag et al. |
| 5,277,711 | A | | 1/1994 | Schmidt et al. |
| 6,488,756 | B1 | | 12/2002 | Schoen et al. |
| 6,620,233 | B1 | | 9/2003 | Seeger et al. |
| 2006/0070552 | A1 | † | 4/2006 | Loch |
| 2006/0225609 | A1 | | 10/2006 | Rueger et al. |
| 2007/0032573 | A1 | † | 2/2007 | Yanagase |
| 2007/0034112 | A1 | | 2/2007 | Mronga et al. |
| 2010/0322981 | A1 | | 12/2010 | Bujard et al. |
| 2011/0051122 | A1 | | 3/2011 | Yang |
| 2011/0237683 | A1 | * | 9/2011 | Schmid et al. ............... 514/770 |
| 2012/0091702 | A1 | † | 4/2012 | Shimizu |
| 2012/0237577 | A1 | † | 9/2012 | Sioss |

FOREIGN PATENT DOCUMENTS

| JP | 2000-211962 A | 8/2000 |
| JP | 2010-083727 A | 4/2010 |
| WO | WO-2007/103812 | 9/2007 |
| WO | 2011/051122 A1 † | 5/2011 |

OTHER PUBLICATIONS

Commission Regulation (EU) No. 231/2012 (Official Journal of the European Union, L83, vol. 55, Mar. 22, 2012), E172 Iron Oxides and Iron Hydroxides.
Communication Pursuant to Article 94(c) EPC in European Application No. 13844126.6, dated May 11, 2017 (6 pages). (018894-0659).
Eckart Effect Pigments, "Technical Data Sheet—SynCrystal Fire-Red," Jul. 2012 (1 page).
International Search Report & Written Opinion in International Application No. PCT/US2013/063245, dated Apr. 10, 2014 (11 pages).
Notification of Reasons for Refusal in JP Application No. 2015-535781, dated Jun. 19, 2017 (English translation—7 pages). (018894-0666).

(Continued)

Primary Examiner — Anna Falkowitz
(74) Attorney, Agent, or Firm — Foley & Lardner LLP

(57) ABSTRACT

An iron oxide containing effect pigment, and methods for producing and using the same are discussed. The iron oxide containing effect pigment may include an iron oxide coating in direct contact with a particulate substrate, which may have high levels of hematite, magnetite, or maghemite; and low amounts of toxic metals. A method for producing the pigment may include chemical vapor deposition of iron pentacarbonyl onto a particulate substrate. The iron oxide containing effect pigments may be incorporated into compositions, such as cosmetics.

23 Claims, No Drawings

(56) References Cited

OTHER PUBLICATIONS

SunShine Effects Synthetic Fluorphlogopite based effect pigments, 10 pages, 2007, SunChemical.†
SunPURO Extra pure inorganic pigments, 8 pages, 2007, SunChemical.†
Commission Regulation (EU) No. 231/2012, 300 pages, Mar. 22, 2012, European Union.†
Technical Data Sheet of SynCrystal Fire-Red, 1 page, Jul. 26, 2012, ECKART Effect pigments.†
Certificate of Analysis, 1 page, Aug. 8, 2012, ECKART Effect Pigments.†

\* cited by examiner
† cited by third party

IRON OXIDE CONTAINING EFFECT PIGMENTS, THEIR MANUFACTURE AND THEIR USE

CROSS-REFERENCE TO RELATED APPLICATIONS

The benefit of the filing date of U.S. Provisional Patent Application No. 61/710,191, filed Oct. 5, 2012 is hereby claimed. The entire disclosure of the aforesaid application is incorporated herein in its entirety by reference.

FIELD OF THE DISCLOSURE

The present disclosure provides iron oxide containing effect pigments, and processes for manufacturing and using the same. The iron oxide containing effect pigment may include a particulate substrate and an iron oxide coating, which may be in direct contact with the particulate substrate and at least partially encapsulates the particulate substrate. The iron oxide containing effect pigment may function as a colorant, and may exhibit an almost angle independent brightness. The process for providing the iron oxide containing effect pigment may include depositing a $Fe_2O_3$-layer from iron pentacarbonyl vapor directly onto a particulate substrate. An advantage of the iron oxide containing effect pigment may be lower levels of toxic metals, such as lead and cobalt, which may be desirable for cosmetic applications, especially in the lip area.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

Effect pigments are typically composed of a plurality of particulate substrates coated with one or more reflecting/transmitting layers. Typically, effect pigments are substrates, such as natural mica or glass, that have been coated with a metal oxide layer. If a colorless metal oxide is used to coat the particulate substrate, then the effect pigment can exhibit a pearl-like luster as a result of the reflection and refraction of light. Further, effect pigments can also exhibit interference color effects. If colored metal oxides are used, then the observed effects depend on reflection, refraction, and absorption.

Effect pigments are known as pearlescent pigments or nacreous pigments, and can be used to impart a pearlescent luster, metallic luster, and/or multi-color effect approaching iridescence, to a material. For example, an effect pigment can be incorporated into a cosmetic or a personal care composition to provide color, iridescence, luster, and/or a pleasing tactile property.

Effect pigments have been produced by depositing iron oxide directly onto substrates, such as mica. However, the deposition of iron oxide using wet techniques, such as the aqueous deposition of $FeCl_3$ to form an iron oxide coating may result in disadvantageous levels of toxic metals, and other impurities. Further, such wet deposition methods typically require calcination of the effect pigments at temperatures in excess of 500° C. When $TiO_2$ is present with $Fe_2O_3$, the high calcination temperature can result in the formation of iron titanate species. Effect pigments have been produced using chemical vapor deposition (CVD) techniques to deposit iron oxide onto substrates. However, the purity of these pigments and the absence of iron titanante formation has not been previously explored or established.

There is an on-going need in the art for iron oxide containing effect pigments having improved properties.

BRIEF SUMMARY

The following embodiments meet and address these needs. The following summary is not an extensive overview. It is intended to neither identify key or critical elements of the various embodiments, nor delineate their scope.

Embodiments discussed herein relate to an iron oxide containing effect pigment, a process for preparing them, and the application of the iron oxide containing effect pigment, for example, in cosmetics. The iron oxide containing effect pigment may comprise a high level of one or more of hematite, magnetite, and maghemite. The effect pigment may comprise substantially no iron titanate. In addition, the iron oxide containing effect pigment disclosed herein may have a low level of heavy metal impurities, such as lead, present in the iron oxide containing effect pigment.

Provided herein is an embodiment of an iron oxide containing effect pigment comprising: a particulate substrate; and an iron oxide coating which can be in direct contact with the particulate substrate and at least partially encapsulates the particulate substrate, wherein the iron oxide coating comprises ≥98% hematite, magnetite, or maghemite; and wherein the iron oxide containing effect pigment comprises: ≤30.0 ppm Ba, ≤15.0 ppm Cr, ≤10.0 ppm Pb, and ≤10.0 ppm Ni. In an embodiment, the particulate substrate can be one or more of natural mica, synthetic mica, $TiO_2$-coated natural mica, $TiO_2$-coated synthetic mica, tin oxide-coated natural mica, tin oxide-coated synthetic mica, silica, alumina, a glass flake, $SiO_2$-coated mica, and $TiO_2$-coated $SnO_x$-coated mica wherein x is 1 or 2. The particulate substrate comprises fluorophlogopite and the iron oxide coating may comprise ≥98% hematite. The particulate substrate can comprise fluorophlogopite; and the iron oxide containing effect pigment can further comprise: ≤2.0 ppm Cd, ≤1.0 ppm Co, ≤20.0 ppm Cu, ≤1.0 ppm Sb, ≤2.0 ppm Se, and ≤70.0 ppm Zn. The iron oxide containing effect pigment can have a diameter from about 10 μm to about 300 μm. The iron oxide coating can have a thickness of from about 1 nm to about 200 nm. The particulate substrate can comprise fluorophlogopite; and the iron oxide coating can comprise ≥98% hematite, magnetite, or maghemite, and wherein the iron oxide containing effect pigment can comprise: ≤12.0 ppm Ba, ≤15.0 ppm Cr, ≤1.0 ppm Pb, and ≤8.0 ppm Ni.

Provided herein is a method of producing an iron oxide containing effect pigment, which can comprise depositing iron oxide from an iron pentacarbonyl vapor directly onto a particulate substrate to form an iron oxide coating on the particulate substrate, wherein the iron oxide coating can be in direct contact with and at least partially encapsulates the substrate, and the iron oxide coating can comprise ≥98% hematite, magnetite, or maghemite; wherein the particulate substrate can be one of natural mica, synthetic mica, $TiO_2$-coated natural mica, $TiO_2$-coated synthetic mica, tin oxide-coated natural mica, tin oxide-coated synthetic mica, silica, alumina, glass flakes, $SiO_2$-coated mica, $TiO_2$-coated $SnO_x$-coated mica, wherein x is 1 or 2; and any combination thereof; and wherein the iron oxide containing effect pigment comprises: ≤30.0 ppm Ba, ≤15.0 ppm Cr, ≤10.0 ppm Pb, and ≤10.0 ppm Ni. In an embodiment, the depositing step can comprise: providing the particulate substrate into a reaction chamber; fluidizing the particulate substrate by pumping a first inert gas into the reaction chamber; heating the reaction chamber to from about 80° C. to about 325° C.; pumping a second gas into the reaction chamber, wherein the second gas comprises oxygen; pumping a third inert gas into the reaction chamber, wherein the third inert gas comprises iron pentacarbonyl; and forming an iron oxide coating on the particulate substrate to produce the iron oxide containing effect pigment. The first inert gas can be pumped in the reaction chamber at a rate of about 1600 l/h to about 2400 l/h. The third inert gas can be pumped in the reaction chamber at a rate of from about 160 l/h to about 240 l/h. The iron oxide coating can have a thickness of from about 1 nm to about 200 nm. The substrate can comprise fluorophlogopite; and the iron oxide containing effect pigment can further comprise: ≤2.0 ppm Cd, ≤1.0 ppm Co, ≤20.0 ppm Cu, ≤1.0 ppm Sb, ≤2.0 ppm Se, and ≤70.0 ppm Zn. The substrate can comprise fluorophlogopite; and the iron oxide coating can comprise ≥98% hematite, magnetite, or maghemite; and wherein the iron oxide containing effect pigment can comprise: ≤12.0 ppm Ba, ≤15.0 ppm Cr, ≤1.0 ppm Pb, and ≤8.0 ppm Ni.

Provided herein is a cosmetic product, which can comprise the iron oxide containing effect pigment described above. In an embodiment, the cosmetic is a cream, emulsion, foam, gel, lotion, milk, mousse, ointment, paste, powder, spray, suspension, or a combination thereof. The cosmetic is selected from the group consisting of: a concealing stick, foundation, stage make-up, mascara, eye shadow, hair color, lipstick, lip gloss, kohl pencil, eye liner, blusher, eyebrow pencil, cream powder, nail enamel, skin glosser stick, hair spray, face powder, leg-makeup, insect repellent lotion, nail enamel remover, perfume lotion, and shampoo.

Provided herein is a method of changing the appearance of skin comprising applying an optically effective amount of the cosmetic, described above, to the skin of an individual in need thereof.

Provided herein is the use of an iron oxide containing effect pigment for the preparation of a cosmetic for improving the look and/or feel of skin.

Provided herein is an iron oxide containing effect pigment, which can comprise: a particulate substrate; and an iron oxide coating which can be in direct contact with the particulate substrate and at least partially encapsulates the particulate substrate, wherein the iron oxide coating can comprise ≥98% hematite, magnetite, or maghemite; and wherein the iron oxide containing effect pigment can comprise: ≤30.0 ppm Ba, ≤15.0 ppm Cr, ≤10.0 ppm Pb, ≤10.0 ppm Ni, and wherein the iron oxide containing effect pigment does not contain pseudobrookite. The particulate substrate comprises fluorophlogopite and the iron oxide coating comprises ≥98% hematite.

It is to be understood that both the foregoing general description and the following detailed description are exemplary and explanatory, and are intended to provide further explanation of the disclosed pigments, methods, and uses.

DETAILED DESCRIPTION

The following definitions apply throughout the specification, unless otherwise noted.

The term "pigment" refers to a solid composition of matter that is colored, and cannot be dissolved in water, acetone, or hexane during one hour.

The term "effect pigment" refers to a pigment that interacts with visible light by reflection and/or transmission and/or refraction.

The term "particulate substrate" refers to a solid composition of matter having a largest dimension below 500 microns.

The phrase "at least partially encapsulates" means that at least about 51% of the surface area of the object partially encapsulated is covered by the encapsulating material.

The term "hematite" refers to $Fe_2O_3$ crystallized according to a trigonal hexagonal (rhombohedral) lattice system. Hematite can also be represented as $\alpha$-$Fe_2O_3$.

The term "maghemite" refers to $\gamma$-$Fe_2O_3$, which crystallizes in the isometric tetartoidal lattice system.

As used herein, "iron titanate" refers to a mixed oxide of iron and titanium of varying ratios. A non-limiting example of an iron titanate is pseudobrookite which has a formula of $Fe_2TiO_5$.

The term "natural mica" means any mica obtained from nature.

The term "synthetic mica" means mica that was created by non-natural means, such as laboratory production. Fluorophlogopite is an exemplary synthetic mica.

The term "diameter" as used herein refers to the largest dimension of a particle, and does not indicate that a particle or particulate substrate is round or spherical or flaky.

The term "about" means ±10% of a number, when this term modifies a number that is not part of a range. The term about means −10% of the lower limit of a numerical range and +10% of the upper limit of the numerical range.

It is understood that any and all whole or partial integers between any ranges set forth herein are included herein.

Unless otherwise stated, all measurements in the specification are in terms of metric units.

Unless otherwise stated, the definite articles "a" and "the" can refer to one, or more than one of the object modified by the definite article.

As envisioned in the present disclosure with respect to the disclosed compositions of matter and methods, in one aspect the embodiments of the disclosure comprise the components and/or steps disclosed therein. In another aspect, the embodiments of the disclosure consist essentially of the components and/or steps disclosed therein. In yet another aspect, the embodiments of the disclosure consist of the components and/or steps disclosed therein.

Embodiments discussed herein relate to an iron oxide containing effect pigment comprising: a particulate substrate; and an iron oxide coating which is in direct contact with the particulate substrate and at least partially encapsulates the particulate substrate. The iron oxide coating may comprise ≥98% hematite, magnetite, or maghemite. The iron oxide coating may also comprise ≤30.0 ppm Ba; ≤15.0 ppm Cr; ≤10.0 ppm Pb; and ≤10.0 ppm Ni.

The particulate substrate may be any solid material that cannot be dissolved in water, acetone, or hexane; has a diameter of from about 3 to about 500 microns; and is smooth enough to allow for interference effects to be observed in the iron oxide containing effect pigment. For example, a suitable substrate includes flaky particles with smooth, substantially flat surfaces. The particulate substrate may be transparent or opaque, including having at least 75% transmission. Examples of suitable materials for the particulate substrate include one or more of: natural mica, synthetic mica, $TiO_2$-coated natural mica, $TiO_2$-coated synthetic mica, tin oxide-coated natural mica, tin oxide-coated synthetic mica, silica, alumina, a glass flake, $SiO_2$-coated mica, and $TiO_2$-coated SnO coated mica wherein x is 1 or 2. However, the materials for the particulate substrate are not limited to the afore mentioned materials. It is understood that any of the aforementioned particulate substrate materials could be coated by one or more layers of another material, such as $TiO_2$ or SnO and $TiO_2$ and the like to form, e.g., $TiO_2$ coated silica. Natural mica may include natural muscovite, natural sericite, and natural phlogopite. Synthetic mica may include synthetic fluorophlogopite. In an embodiment, the particulate substrate comprises fluorophlogophite having less than 5 parts-per-million (ppm) of As, Ba, Cd, Co, Cu, Hg, Ni, Pb, Sb, Se, and/or Zn, including less than 1 ppm As, Cd, Hg, Pb, and/or Sb.

It has been found that the purity of the iron oxide containing effect pigments may be influenced by the toxic metal content of both the iron oxide coating, the particulate substrate, and the process used to deposit the iron oxide coating. For instance, and without wishing to be bound by any particular theory, a low metal content in synthetic mica may combine with the choice of deposition method, such as CVD, to produce iron oxide containing effect pigments having extremely low amounts of toxic metal contaminants. Accordingly, one advantage of an iron oxide containing effect pigment comprising synthetic mica as a particulate substrate may be lower levels of metal content, relative to natural mica. For example, one type of synthetic mica is fluorophlogopite. By controlling the purity levels of each starting material and using a CVD deposition step, it has been discovered that iron oxide containing effect pigments having an advantageously low toxic metal content may be produced.

In some embodiments, the particulate substrate includes synthetic fluorophlogopite, which has been found to have a benefit of high purity. In an embodiment, the particulate substrate includes glass flakes (borosilicate), which produce higher chroma pigments. In other embodiments, the particulate substrates can include synthetic alumina and silica, which have a benefit of a smoother surface. In an embodiment, natural mica serve as the particulate substrate as least expensive source material.

The particulate substrate used in the present disclosure may be irregularly shaped. Nevertheless, the particulate substrate will be referred to herein as having a "diameter", wherein the diameter refers to the largest dimension of the particle. The particulate substrate may have an average diameter of from about 10 microns to 300 microns, from 15 to 250 microns, or from 20 to 150 microns. The particulate substrate may also have an aspect ratio of greater than about 5. The specific surface area (BET) of the particulate substrate may range from about 0.2 to 25 $m^2/g$, including 2-15 $m^2/g$. However, it is understood that a suitable diameter, aspect ratio, and/or specific surface area of the particulate substrate may be selected based on the intended use.

Embodiments of the iron oxide coating may include ≥98% hematite, magnetite, or maghemite, or may include ≥99%, or may include ≥99.5% hematite, magnetite, or maghemite. In an embodiment, the thickness of the iron oxide coating may range from about 1 nm to about 200 nm, from about 20 nm to about 150 nm, or from about 25 to 150 nm. The thickness of the coating is not particularly limited, so long as the thickness allows for a range of interference colors to be observed. By adjusting the thickness of the iron oxide layer, the iron oxide effect pigment may exhibit interference colors, including bronze, copper, russet and others known in the art.

In an embodiment, the iron oxide coating may be in direct contact with a particulate substrate and may at least partially encapsulate the particulate substrate. In another embodiment, an average of at least 95% of the iron oxide coating may be in direct contact with the particulate substrate. In another embodiment, the iron oxide coating may encapsulate an average of at least 60% of the surface area of the particulate substrate, an average of at least 75% of the surface area, or an average of at least about 95% of the surface area of the particulate substrate.

In an embodiment, the iron oxide containing effect pigment may be characterized by having low amounts of toxic metals. As used herein, "toxic metals" refers to metals such as As, Ba, Cd, Co, Cu, Hg, Ni, Pb, Sb, Se, and/or Zn. In an embodiment, toxic metals refers to As, Ba, Cd, Co, Cu, Hg, Ni, Pb, Sb, Se, and/or Zn. For example, in an embodiment, the iron oxide effect pigment may comprise:

1.0-5.0 ppm As, including 1.5-3.0 ppm As;
1.0-30.0 ppm Ba, including 3.0-11.0 ppm Ba;
0.05-15.0 ppm Cr, including 2.0-7.0 ppm Cr;
0.01-10.0 ppm Pb, including 0.05-5.0 ppm Pb;
1.0-10.0 ppm Ni, including 1.5-3.0 ppm Ni;
0.01-2.0 ppm Cd, including 0.05-0.25 ppm Cd;
0.1-1.0 ppm Co, including 0.2-0.50 ppm Co;
1.0-20.0 ppm Cu, including 2.0-12.0 ppm Cu;
0.01-1.0 ppm Sb, including 0.05-0.85 ppm Sb;
0.1-2.0 ppm Se, including 0.2-1 ppm Se; and/or
1.0-70.0 ppm Zn, including 5.0-50.0 ppm Zn.

In an embodiment, the iron oxide coating and/or iron oxide containing effect pigment may be further characterized as containing ≤1.0 ppm iron titanate. In another embodiment, the iron oxide containing effect pigment may contain no iron titanante. In another embodiment, the iron oxide containing effect pigment may contain no pseudobrookite.

In an embodiment, the particulate substrate may be fluorophlogopite, and the iron oxide effect pigment may comprise:

1.0-12.0 ppm Ba, including 3.0-11.0 ppm Ba;
0.05-15.0 ppm Cr, including 2.0-7.0 ppm Cr;
0.01-1.0 ppm Pb, including 0.05-0.5 ppm Pb, and/or
1.0-10.0 ppm Ni, including 1.5-7.0 ppm Ni; and
the iron oxide coating comprises: ≥98% hematite, magnetite, or maghemite, including ≥99%, including 99.5%.

Without wishing to be bound to any particular theory, it is believed that the low amounts of toxic metal in the iron oxide containing effect pigment disclosed herein may result from the combination of the purity of the particulate substrate and the CVD deposition of distilled iron pentacarbonyl. For example, when fluorophlogopite is used as the particulate substrate, then the CVD deposition of iron pentacarbonyl can avoid lead contamination due to the low levels of trace amounts of lead in the synthetic mica, the iron pentacarbonyl, and the procedure for reacting the two in a lead free CVD reaction chamber. In an embodiment, an iron oxide containing pigment contains ≤1 ppm lead, including ≤0.3 ppm lead. An advantage of the iron oxide containing effect pigment may be its extremely low lead content. To avoid the harmful effects of lead, it is desirable to lower the amount of lead in contact with skin, especially in the lip area, as much as possible.

Embodiments herein also relate to a method of producing an iron oxide containing effect pigment. The method comprises depositing an iron pentacarbonyl vapor directly onto a particulate substrate to form an iron oxide coating on the particulate substrate. The particulate substrate may be one of natural mica, synthetic mica, $TiO_2$-coated natural mica, $TiO_2$-coated synthetic mica, tin oxide-coated natural mica, tin oxide-coated synthetic mica, silica, alumina, glass flakes, $SiO_2$-coated mica, $TiO_2$-coated $SnO_x$ coated mica, wherein x is 1 or 2; and any combination thereof. The iron oxide coating deposited may be in direct contact with and may at least partially encapsulates the substrate. The resulting iron oxide coating may comprise ≥98% hematite, magnetite, or maghemite. The resulting iron oxide containing effect pigment may comprise:

≤30.0 ppm Ba,
≤15.0 ppm Cr,
≤10.0 ppm Pb, and
≤10.0 ppm Ni.

In an embodiment of the method, the deposition step further includes: providing the particulate substrate into a reaction chamber; fluidizing the particulate substrate by pumping a first inert gas into the reaction chamber; heating the reaction chamber to from about 80° C. to about 325° C.; and pumping a second gas and an third inert gas into the reaction chamber, wherein the third inert gas comprises iron pentacarbonyl; and forming an iron oxide coating on the particulate substrate to produce the iron oxide containing effect pigment.

In an embodiment, the depositing step may take place as a chemical vapor deposition (CVD) technique, when an iron pentacarbonyl vapor can be directly deposited onto a particulate substrate to form an iron oxide coating that at least partially encapsulates the particulate substrate. In an embodiment, the choice of particulate substrate for the deposition step is not particularly limited, and can include at least one of natural mica, synthetic mica, $TiO_2$-coated natural mica, $TiO_2$-coated synthetic mica, tin oxide-coated natural mica, tin oxide-coated synthetic mica, silica, alumina, glass flakes, $SiO_2$-coated mica, $TiO_2$-coated $SnO_x$ coated mica, wherein x is 1 or 2; and any combination thereof. Tin oxide may or may not be present where titanium dioxide is present. A benefit of tin oxide can be that a tin oxide coating functions as a rutile crystal director for $TiO_2$. A tin oxide coating can also act as an adhesion promoter on a substrate.

One advantage of using iron pentacarbonyl during the deposition step may be that iron pentacarbonyl is capable of being distilled to remove toxic metals, such as lead. Further, the chemical vapor deposition of iron pentacarbonyl avoids the introduction of impurities into the iron oxide containing effect pigment.

In an embodiment, the providing step is not particularly limited, so long as the providing step introduces the particulate substrate into a reaction chamber. For example, a CVD reactor may include a hollow vessel having at least one gas flow into and out of the vessel, as well as a heat source for heating the hollow vessel.

The step of fluidizing the particulate substrate by pumping a first gas into the reaction chamber is not particularly limited, so long as the flow of the first gas can move the particulate substrate around the interior of the reaction chamber. Forcing a gas to move the particles in such a fluid-like manner is known as "fluidizing" the particles. An advantage of fluidizing the plurality of particulate substrate prior to introduction of the iron pentacarbonyl, is that the fluid flow of the particles allows for the particles to be evenly coated in the deposition step.

In an embodiment, the first inert gas is pumped in the reaction chamber at a rate of about 1600 l/h to about 2400 l/h, including from about 1800 to about 2200 l/h. In an embodiment, the first inert gas is pumped in the reaction chamber at a rate of about 2 $m^3$/h to about 200 $m^3$/h, or at a rate of about 5 to 100 $m^3$/h. In an embodiment, the inert gas is not particularly limited, so long as the inert gas does not react with the iron pentacarbonyl, the particulate substrate, or the iron containing effect pigment. For example, suitable inert gases may include nitrogen, helium, argon, carbon monoxide, carbon dioxide and other inert gases known in the art.

In an embodiment, the step of heating the reaction chamber is not particularly limited, so long as the temperature inside the reaction chamber can be maintained at from about 80° C. to about 325° C. during the duration of the deposition step and/or step of forming an iron oxide coating step, including about 100° C. to about 275° C., including 125° C. to 250° C. Heating the reaction chamber may facilitate the reaction of the iron pentacarbonyl and the particulate substrate to form the iron oxide containing effect pigment.

In an embodiment, the step of pumping a second gas into the reaction chamber, wherein the second gas comprises oxygen, is not particularly limited so long as the second gas allows provides enough oxygen to allow for decomposition of iron carbonyl once the third inert gas is added to the reaction chamber. In an embodiment, the second gas can comprise oxygen, water vapor, and an inert gas, such as nitrogen, helium, argon, carbon monoxide, carbon dioxide and other inert gases known in the art. In another embodiment, the second gas can comprise air, water vapor, and an inert gas, such as nitrogen, helium, argon, carbon monoxide, carbon dioxide and other inert gases known in the art. For example, a mixture of air and an inert gas, such as nitrogen, can be pumped through water to provide a second gas comprising, oxygen and water vapor.

The step of pumping a second gas into the reaction chamber can proceed before, during, or after the step of pumping a third gas into the reaction chamber.

In an embodiment, the step of pumping a third inert gas into the reaction chamber, wherein the inert gas comprises iron pentacarbonyl is not particularly limited, so long as the iron pentacarbonyl is introduced into the reaction chamber at a controlled rate. In an embodiment, the third inert gas may be nitrogen, neon, argon, carbon monoxide, carbon dioxide, or other inert gases known in the art. In an embodiment, the third inert gas is pumped into the reaction chamber at a rate of from about 160 l/h to about 240 l/h, including from about 180 to about 220 l/h. In an embodiment, the third inert gas is pumped into the reaction chamber at a rate of from about 2 $m^3$/h to about 30 $m^3$/h, from about 5 to about 25 $m^3$/h, or from about 10 to about 20 $m^3$/h. In an embodiment, the third inert gas may be saturated with iron pentacarbonyl. In an embodiment, the the third inert gas includes at least about 10 vol. % iron pentacarbonyl. In an embodiment, the third inert gas includes 30 vol. % iron pentacarbonyl.

The thickness and properties of the iron oxide coating depends on the composition of the third inert gas, the rate the third inert gas is pumped into the reaction chamber, and the duration and temperature of this step. The primary control of the thickness parameter is provided by the rate and duration of the iron pentacarbonyl addition.

The step of forming an iron oxide coating directly on the particulate substrate to produce the iron oxide containing effect pigment is not particularly limited, so long as the iron pentacarbonyl in the reaction chamber can form an iron oxide coating that at least partially encapsulates the particulate substrate. In an embodiment, the step for forming the iron oxide coating can be maintained at from about 80° C. to about 325° C. during the duration of the forming step. Exemplary temperature ranges during the forming step also include about 100° C. to about 275° C. and about 125° C. to 250° C. In an embodiment, the step for forming the iron oxide coating occurs while the first and third inert gases are pumped into the reaction chamber, such that the iron oxide coating is directly deposited onto the surface of the particulate substrate while the particles are fluidized.

In an embodiment, the method for producing the iron oxide containing effect pigment may advantageously provide iron oxide containing effect pigments characterized by having low amounts of toxic metals, such as As, Ba, Cd, Co, Cu, Hg, Ni, Pb, Sb, Se, and/or Zn. For example, in an embodiment, the iron oxide effect pigment comprises:
1.0-5.0 ppm As, including 1.5-3.0 ppm As;
1.0-30.0 ppm Ba, including 3.0-11.0 ppm Ba;
0.05-15.0 ppm Cr, including 2.0-7.0 ppm Cr;
0.01-10.0 ppm Pb, including 0.05-5.0 ppm Pb;
1.0-10.0 ppm Ni, including 1.5-3.0 ppm Ni;
0.01-2.0 ppm Cd, including 0.05-0.25 ppm Cd;
0.1-1.0 ppm Co, including 0.2-0.50 ppm Co;
1.0-20.0 ppm Cu, including 2.0-12.0 ppm Cu;
0.01-1.0 ppm Sb, including 0.05-0.85 ppm Sb;
0.1-2.0 ppm Se, including 0.2-1 ppm Se; and/or
1.0-70.0 ppm Zn, including 5.0-50.0 ppm Zn.

In an embodiment, the method may produce iron oxide containing effect pigments characterized as containing no iron titanate. In another embodiment, the procedure may produce iron oxide coating and/or an iron oxide containing effect pigment contain ≤1.0 ppm iron titanate. One advantage of an embodiment of the process may be that ≤1.0 ppm or zero detectable pseudobrookite can form. In an embodiment, iron titanate phases are lower than 0.5% or iron titanate, when analyzed by powder diffraction x-ray analysis. In contrast, when iron oxide films undergo a calcination step in the presence of titanium dioxide, the high temperature of calcination may result in the formation of iron titanante. Iron titanate can be disadvantageous because its presence in, e.g., cosmetic applications, may be questioned in terms of its function in the formulation.

In an embodiment of the method, when fluorophlogopite serves as the particulate substrate, then the iron oxide effect pigment may comprise:
1.0-12.0 ppm Ba, including 3.0-11.0 ppm Ba;
0.05-15.0 ppm Cr, including 2.0-7.0 ppm Cr;
0.01-1.0 ppm Pb, including 0.05-0.5 ppm Pb, and/or
1.0-10.0 ppm Ni, including 1.5-7.0 ppm Ni; and
the iron oxide coating comprises: ≥98% hematite, magnetite, or maghemite, including ≥99%, or ≥99.5%.

In an embodiment, the iron oxide containing effect pigment comprises single layer of $Fe_2O_3$. However, it is understood that other layers can be added provided that they have different refractive indices, which are capable of functioning as an effect pigment.

It is contemplated that a cosmetic product can include the iron oxide effect pigment discussed herein. An advantage of a cosmetic product, including lipstick and lip gloss, can be that low levels of toxic metals are introduced into the lip area. In an embodiment, the cosmetic product can be a cream, emulsion, foam, gel, lotion, milk, mousse, ointment, paste, powder, spray, suspension, or a combination thereof. The type of cosmetic can include a concealing stick, foundation, stage make-up, mascara, eye shadow, hair color, lipstick, lip gloss, kohl pencil, eye liner, blusher, eyebrow pencil, cream powder, nail enamel, skin glosser stick, hair spray, face powder, leg-makeup, insect repellent lotion, nail enamel remover, perfume lotion, and shampoo, as well as other cosmetics known in the art. For a review of cosmetic applications, see COSMETICS: SCIENCE AND TECHNOLOGY, 2nd Ed., Eds: M. S. Balsam and Edward Sagarin, Wiley-Interscience (1972), and deNavarre, THE CHEMISTRY AND SCIENCE OF COSMETICS, 2nd Ed., Vols. 1 and 2 (1962), Van Nostrand Co. Inc., Vols. 3 and 4 (1975), Continental Press, both of which are hereby incorporated by reference.

The amount of iron oxide containing pigment present in a cosmetic composition is dependent on the cosmetic being created and the final form of the cosmetic. One skilled in the art will be able to determine the appropriate amount of pigment to use based upon the desired properties of the cosmetic formulation; however, a cosmetic composition can comprise from about 0.005 to 99.9%, about 0.05 to about 50%, or about 0.1 to about 10% by weight of the iron oxide containing pigment, based on the total weight of the cosmetic composition.

The cosmetic composition optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous, or antiallergic active ingredients and mixtures thereof. Cosmetic formulations are known in the art. See, for instance, US Publication Nos. 20080196847 and 20100322981.

Methods of applying embodiments of a cosmetic that includes iron oxide effect pigments discussed herein are not particularly limited, so long as the methods apply an optically effective amount of the cosmetic discussed herein to the skin of an individual in need thereof. It is understood that an optically effective amount is an amount capable of being detected by the human eye.

EXAMPLES

The products, compositions and methods are further described in detail by reference to the following experimental examples. These examples are provided for purposes of illustration only, and are not intended to be limiting unless otherwise specified. Thus, the products, compositions and methods of the disclosure should in no way be construed as being limited to the following examples, but rather, should be construed to encompass any and all variations which become evident as a result of the teaching provided herein.

Example 1

Coating of D-Mica with $Fe_2O_3$ 600 g of a filter cake material of d-mica were first heat treated at 110° C. and then de-agglomerated using a rotating blade mixer. The treated material was fed in a fluidized bed reactor with a height of 100 cm and an inner diameter of 15 cm. To keep the fluidization about 2000 l/h $N_2$ were pumped into the reactor either as gas needed for fluidization or to bring in the needed chemical compounds. The temperature was then increased to 184° C. inner temperature. By means of by-passes, 150 l/h air diluted with 1000 l/h $N_2$ and 400 l/h water wet nitrogen (the nitrogen were pumped through a 50° C. water bath before going to the reactor) were added continuously after reaching the temperature of 174° C. After reaching constant parameters for fluidization and temperature, $Fe(CO)_5$ was fed through a nitrogen gas stream of 200 l/h which result in a $Fe(CO)_5$ amount of 30-50 ml/h. During 20 h, 1050 ml $Fe(CO)_5$ were fed into the reactor. The color progression was evaluated by taking out samples. After reaching a red color, the dosing of $Fe(CO)_5$ was stopped. The reactor was cooled down to room temperature and an amount of 1185 g of iron-oxide-coated mica was taken out from the reactor.

Example 2

Coating of Synthetic Mica (Phlogopit) with $Fe_2O_3$ 1000 g of synthetic mica were fed in a fluidized bed reactor with a height of 100 cm and an inner diameter of 15 cm. To keep the fluidization about 2000 l/h $N_2$ were pumped into the reactor either as gas needed for fluidization or to bring in the needed chemical compounds. The temperature was then increased to 182° C. inner temperature. By means of by-passes, 150 l/h air diluted with 1000 l/h $N_2$ and 400 l/h water wet nitrogen (the nitrogen were pumped through a 50° C. water bath before going to the reactor) were added continuously after reaching the temperature of 178° C. After reaching constant parameters for fluidization and temperature $Fe(CO)_5$ was fed through a nitrogen gas stream which result in a $Fe(CO)_5$ amount of 30-50 ml/h. During 20.5 h 1560 ml $Fe(CO)_5$ were fed into the reactor. The color progression was evaluated by taking out samples. After reaching a red color, the dosing of $Fe(CO)_5$ was stopped. The reactor was cooled down to room temperature and an amount of 1807 g of iron-oxide-coated mica was taken out from the reactor.

Example 3

Coating of "z"-Mica with $Fe_2O_3$ 600 g of synthetic mica were fed in a fluidized bed reactor with a height of 100 cm and an inner diameter of 15 cm. To keep the fluidization about 2000 l/h $N_2$ were pumped into the reactor either as gas needed for fluidization or to bring in the needed chemical compounds. The temperature was then increased to 174° C. inner temperature. By means of by-passes, 150 l/h air diluted with 1000 l/h $N_2$ and 400 l/h water wet nitrogen (the nitrogen were pumped through a 50° C. water bath before going to the reactor) were added continuously after reaching the temperature of 173° C. After reaching constant parameters for fluidization and temperature $Fe(CO)_5$ was fed through a nitrogen gas stream which result in a $Fe(CO)_5$ amount of 30-50 ml/h. During 15.5 h 710 ml $Fe(CO)_5$ were feed into the reactor. The color progression was evaluated by taking out samples. After reaching a red color, the dosing of $Fe(CO)_5$ was stopped. The reactor was cooled down to room temperature and an amount of 961 g of iron-oxide-coated mica was taken out from the reactor.

Samples of Examples 1, 2 and 3 were analyzed using elemental analysis techniques appropriate for each metal. The technique used for As, Cd, Cr, Co, Ni, Pb, Se, Sb was Inductively-Coupled Plasma Mass Spectrometry (ICP-MS), while Ba, Zn, Cu were analyzed using Inductively-Coupled Plasma Optical Emission Spectroscopy (ICP-OES). Mercury (Hg) was analyzed using Cold Vapor Atomic Absorption spectroscopy. The data are in Table 1.

TABLE 1

| Amount of Toxic Metal in Particulate Substrate (ppm) | Example 1 (synthetic mica) (ppm) | Example 2 (natural mica D) (ppm) | Example 3 (natural mica Z) (ppm) |
| --- | --- | --- | --- |
| Arsenic | <1.01 | 0.28 | 0.65 |
| Barium | 1.1 | 26 | 6.2 |
| Cadmium | <1.01 | <0.22 | <0.22 |
| Cobalt | <4.05 | 0.9 | 0.65 |
| Chromium | <4.05 | 14.0 | 9.5 |
| Copper | <4.05 | 1.8 | 1.5 |
| Mercury | <0.04 | <0.04 | <0.04 |
| Nickel | <4.05 | 1.5 | 1.5 |
| Lead | <1.01 | 8.0 | 3.1 |
| Antimony | <1.01 | 9.4 | <0.22 |
| Selenium | <4.05 | <0.87 | <0.89 |
| Zinc | <4.05 | 69 | 37 |

Table 2 shows a comparison between the total dissolution data of several samples coated via CVD and the traditional aqueous route on a number of materials. Both synthetic and natural mica were used as substrates. All CVD coated samples show a distinctly lower heavy metal profile compared to the samples coated via the aqueous route in several elements, namely Ba, Co, Cr and Ni. The other element levels are comparable for both methods.

TABLE 2

| Amount of Toxic Metal in Iron Oxide Containing Effect Pigments | Example 1 (CVD on synthetic mica) (ppm) | Example 2 (CVD on natural mica) (ppm) | Example 3 (CVD on natural mica) (ppm) | Example 4 (Aqueous on natural mica) (ppm) | Example 5 (Aqueous on natural mica) (ppm) |
| --- | --- | --- | --- | --- | --- |
| Arsenic | 3.1 | 2.3 | 3.6 | 4.0 | 1.8 |
| Barium | 11.0 | 27.0 | 11.0 | 117.5 | 47.0 |
| Cadmium | <0.25 | <0.25 | <0.25 | 1.7 | <0.2 |
| Cobalt | 0.35 | 0.48 | 0.76 | 99.8 | 19.0 |
| Chromium | 14.0 | 6.1 | 6.5 | 31.9 | 19.0 |
| Copper | 7.49 | 11.5 | 15.2 | 9.5 | 6.7 |
| Mercury | <0.10 | <0.10 | <0.10 | 1.6 | <0.04 |
| Nickel | 6.1 | 2.3 | 2.6 | 32.7 | 50.0 |
| Lead | 0.30 | 8.6 | 4.5 | <4 | 5.9 |
| Antimony | <0.25 | <0.25 | <0.25 | 2.0 | <0.2 |
| Selenium | 0.83 | 0.72 | 1.00 | 4.0 | <0.90 |
| Zinc | 47 | 67 | 68 | 55.1 | 55.0 |

When comparing the iron penta-carbonyl coated samples amongst each other, surprisingly the synthetic mica sample shows higher levels of Cr and Ni than the other two samples, and distinctly lower levels of Cu, Pb and Zn.

As can be seen from Table 1, synthetic mica provides some advantages in heavy metal levels, especially in the levels of Ba, Cr, Pb and Zn.

Example 4

Crème Lipstick

To produce a lipstick all of Phase A ingredients were weighed in a vessel and heated to 85±3° C., stirring until melted and uniform. Phase B was pre-dispersed and added to Phase A, maintaining temperature at 82±3° C. for 30 minutes with gentle agitation. The mixture was cooled to 75±3° C. and fragrance added. The mass was then poured into a container or components. See Table 3.

TABLE 3

| Phase | Ingredients | % w/w |
|---|---|---|
| A. | *Crambe Abyssinica* Seed Oil (FANCOR ABYSSINIAN OIL) [1] (q.s to 100%) | 17.86 |
| | *Euphorbia Cerifera* (*Candelilla*) Wax (*Candelilla* Wax SP 75) [2] | 3.00 |
| | Copernicia Cerifera (Carnauba) Wax (Carnauba Wax SP 63) [2] | 1.50 |
| | Beeswax (Beeswax White SP 422) [2] | 1.00 |
| | Ceresine (Ceresine Wax White SP 252) [2] | 6.00 |
| | Microcrystalline Wax (MULTIWAX 180-W) [2] | 1.50 |
| | Oleyl Alcohol (NOVOL) [3] | 3.00 |
| | Isosteryl Palmitate (JEECHEM ISP) [4] | 4.25 |
| | Caprylic/Capric Triglyceride | 8.25 |
| | Bis-Diglyceryl Polyacyladipate-2 (SOFTISAN 649) [5] | 2.00 |
| | Acetylated Lanolin Alcohol (JEELAN MOD) [4] | 2.50 |
| | Sorbitan Tristearate (JEECHEM STS) [4] | 1.75 |
| | Ozokerite (Ozokerite Wax White SP 1026) [2] | 6.75 |
| | Glyceryl Monolaurate (ULTRAPURE GML) [6] | 1.00 |
| | Antioxidants | q.s. |
| | Preservatives | q.s. |
| | UV Absorbers | q.s. |
| B. | Meadowfoam Estolide (MEADOWESTOLIDE) [2] | 2.00 |
| | Pentaerythrityl Tetraisostearate (CRODAMOL PTIS) [3] | 6.00 |
| C. | *Crambe Abyssinica* Seed Oil (FANCOR ABYSSINIAN OIL) [1] | 20.00 |
| | Red 21* | 1.14 |
| | GV32085-068 (Synthetic mica coated with iron oxide via CVD) [7] | 10.50 |
| D. | Fragrance | q.s. |

Suppliers and Trademark Owners
[1] Fancor Ltd.
[2] Strahl & Pitsch, Inc.
[3] CRODA
[4] Jeen International Corporation
[5] SASOL
[6] Ultra Chemical, Inc.
[7] BASF

Example 5

Cream Foundation

A cream foundation formulation is shown in Table 4. DI Water and MPDIOL Glycol were added to the main vessel and homogenization was started. VEEGUM was sprinkled in and homogenized until uniform. Then KELTROL CG-T was sprinkled in and homogenized until uniform. In a separate container, all of Phase B was heated to 60-70° C. and mixed until uniform. Under homogenization Phase B was added to Phase A at 70° C. Phase C was pulverized in appropriate blending equipment and added to Phase AB under homogenization until uniform color was achieved. The mass was transferred to sweep mixing and cooled to 40° C.

DI Water and MPDIOL Glycol were added to the main vessel and homogenization was started. VEEGUM was sprinkled in and homogenized until uniform. Then KELTROL CG-T was sprinkled in and homogenized until uniform. In a separate container, all of Phase B was heated to 60-70° C. and mixed until uniform. Under homogenization Phase B was added to Phase A at 70° C. Phase C was pulverized in appropriate blending equipment and added to Phase AB under homogenization until uniform color was achieved. The mass was transferred to sweep mixing and cooled to 40° C.

TABLE 4

| Phase | Ingredients | % w/w |
|---|---|---|
| A. | DI Water (q.s to 100%) | 60.60 |
| | Methylpropanediol (MPDIOL Glycol) [1] | 5.00 |
| | Magnesium Aluminum Silicate (VEEGUM) [2] | 0.60 |
| | Xanthan Gum (KELTROL CG-T) [3] | 0.40 |
| B. | Cetearyl Olivate (and) Sorbitan Olivate (OLIVEM 1000) [4] | 4.00 |
| | Hydrogenated Olive Oil (and) Olea Europaea (Olive) Fruit Oil (and) Olea Europaea (Olive) Oil Unsaponifiables (OLIWAX) [4] | 2.00 |
| | Caprylic/Capric Triglyceride (and) Di-PPG-3 Myristyl Ether Adipate (and) Sorbitan Isostearate (CRODASPERSE) [5] | 7.00 |
| | Meadowfoam Estolide (and) Meadowfoam Delta-Lactone (MEADOWDERM 100) [6] | 2.00 |
| | Isodecyl Neopentanoate (CERAPHYL SLK) [7] | 5.00 |
| | Antioxidants | q.s. |
| | Preservatives | q.s. |
| C. | Kaolin (HUBER 90) [8] | 0.50 |
| | Polymethyl Methacrylate (PMMA H) [9] | 4.00 |
| | Mearlmica ® SVA (Mica (and) Lauroyl Lysine) [10] | 3.00 |
| | GV32085-068 (Synthetic mica coated with iron oxide via CVD) [10] | 5.52 |

Suppliers and Trademark Owners
[1] Lyondell Chemical Company
[2] RT Vanderbilt, Inc
[3] CP Kelco
[4] B&T Company
[5] CRODA
[6] Fancor Ltd.
[7] ISP
[8] J.M. Huber Corporation
[9] Brenntag Specialties, Inc
[10] BASF

Example 6

Nail Enamel

Table 5 shows a nail enamel formula. To produce the nail enamel, Phase A was added to an appropriate size vessel fitted with a propeller mixer. Phase B was added to Phase A while mixing until batch was uniform. The mass was then filled into containers.

TABLE 5

| Phase | Ingredients | % w/w |
|---|---|---|
| A | Nail Enamel Base (Butyl Acetate (and) Toluene (and) Nitrocellulose (and) Tosylamide/Formaldehyde Resin (and) Isopropyl Alcohol (and) Dibutyl Phthalate (and) Ethyl Acetate (and) Camphor (and) n-Butyl Alcohol (and) Silica (and) Quaterinum-18 Hectorite) | 97.90 |
| B. | Iron Oxides (Black, 4.0-6.0% Toluene Free/Formaldehyde Free Color Solutions) | 0.10 |
| | Flamenco ® Winter Sparkle 130Q (Mica (and) Titanium Dioxide) [1] | 0.75 |
| | GV32085-068 (Synthetic mica coated with iron oxide via CVD) [1] | 1.25 |

Suppliers and Trademark Owners
[1] BASF

All patents and publications referred to in the application are herein incorporated by reference in their entirety for all purposes. While the products, methods of making them, and their methods of use have been disclosed with reference to specific embodiments, it is apparent that other embodiments and variations may be devised by others skilled in the art without departing from the true spirit and scope of the described products and methods. The appended claims are intended to be construed to include all such embodiments and equivalent variations.

What is claimed is:

1. An iron oxide containing effect pigment comprising:
   a particulate substrate; and
   an iron oxide coating which is in direct contact with the particulate substrate and at least partially encapsulates the particulate substrate;
   wherein:
      the iron oxide coating comprises >98% hematite, magnetite, or maghemite; and
      the iron oxide containing effect pigment comprises ≤15.0 ppm Cr, based on the total iron oxide containing effect pigment as determined by total dissolution.

2. The iron oxide containing effect pigment of claim 1, wherein the particulate substrate is one or more of natural mica, synthetic mica, $TiO_2$-coated natural mica, $TiO_2$-coated synthetic mica, tin oxide-coated natural mica, tin oxide-coated synthetic mica, silica, alumina, a glass flake, $SiO_2$-coated mica, and $TiO_2$-coated $SnO_x$-coated mica wherein x is 1 or 2.

3. The iron oxide containing effect pigment of claim 1, wherein the particulate substrate comprises synthetic mica.

4. The iron oxide containing effect pigment of claim 1, wherein the iron oxide containing effect pigment has a diameter from about 10 μm to about 300 μm.

5. The iron oxide containing effect pigment of claim 3, wherein the particulate substrate comprises fluorophlogopite.

6. A method of producing an iron oxide containing effect pigment, the method comprising:
   depositing iron oxide from an iron pentacarbonyl using chemical vapor deposition directly onto a particulate substrate to form an iron oxide coating on the particulate substrate;
   wherein:
      the iron oxide coating is in direct contact with and at least partially encapsulates the substrate, and the iron oxide coating comprises:
         >98% hematite, magnetite, or maghemite; and
      the iron oxide containing effect pigment comprises:
         ≤15.0 ppm Cr, based on the total iron oxide containing effect pigment as determined by total dissolution.

7. The method of claim 6, wherein the depositing step comprises:
   providing the particulate substrate into a reaction chamber;
   fluidizing the particulate substrate by pumping a first inert gas into the reaction chamber;
   heating the reaction chamber to from about 80° C. to about 325° C.;
   pumping a second gas into the reaction chamber, wherein the second gas comprises oxygen;
   pumping a third inert gas into the reaction chamber, wherein the third inert gas comprises iron pentacarbonyl; and
   forming an iron oxide coating on the particulate substrate to produce the iron oxide containing effect pigment.

8. The method of claim 7, wherein the first inert gas is pumped in the reaction chamber at a rate of about 1600 l/h to about 2400 l/h.

9. The method of claim 7, wherein the third inert gas is pumped in the reaction chamber at a rate of from about 160 l/h to about 240 l/h.

10. The method of claim 6, wherein the iron oxide coating has a thickness of from about 1 nm to about 200 nm.

11. The method of claim 6, wherein the substrate comprises fluorophlogopite.

12. A cosmetic product comprising the iron oxide containing effect pigment of claim 1.

13. The cosmetic of claim 12, wherein the cosmetic is a cream, emulsion, foam, gel, lotion, milk, mousse, ointment, paste, powder, spray, suspension, or a combination thereof.

14. The cosmetic of claim 12, wherein the cosmetic is selected from the group consisting of: a concealing stick, foundation, stage make-up, mascara, eye shadow, hair color, lipstick, lip gloss, kohl pencil, eye liner, blusher, eyebrow pencil, cream powder, nail enamel, skin glosser stick, hair spray, face powder, leg-makeup, insect repellent lotion, nail enamel remover, perfume lotion, and shampoo.

15. The iron oxide containing effect pigment of claim 1 wherein the iron oxide containing effect pigment does not contain pseudobrookite.

16. The iron oxide containing effect pigment of claim 1 formed by a chemical vapor deposition method, comprising:
   fluidizing a particulate substrate in a reaction chamber with a first inert gas;
   heating the reaction chamber;
   pumping a second gas into the reaction chamber, the second gas including i) oxygen, water vapor, and a second inert gas, or ii) air, water vapor, and a second inert gas; and
   pumping a third inert gas including iron pentacarbonyl into the reaction chamber to form a distilled iron pentacarbonyl that reacts with the particulate substrate to form an iron oxide coating on the particulate substrate.

17. An iron oxide containing effect pigment consisting of:
   a particulate substrate selected from the group consisting of one or more of natural mica, synthetic mica, $TiO_2$-coated natural mica, $TiO_2$-coated synthetic mica, tin oxide-coated natural mica, tin oxide-coated synthetic mica, silica, alumina, $SiO_2$-coated mica, and $TiO_2$-coated $SnO_x$-coated mica wherein x is 1 or 2; and
   an iron oxide coating which is in direct contact with the particulate substrate and at least partially encapsulates the particulate substrate;
   wherein:
      the iron oxide coating is deposited on the particulate substrate using chemical vapor deposition and the iron oxide coating comprises >98% hematite, magnetite, or maghemite; and
      the iron oxide containing effect pigment comprises:
         ≤30.0 ppm Ba,
         ≤15.0 ppm Cr,
         ≤10.0 ppm Pb, and
         ≤10.0 ppm Ni,
         based on the total iron oxide containing effect pigment as determined by total dissolution.

18. An iron oxide containing effect pigment of claim 17, wherein: the particulate substrate consists of synthetic mica.

19. The iron oxide containing effect pigment of claim 1, wherein the iron oxide containing effect pigment further comprises ≤30.0 ppm Ba; ≤10.0 ppm Pb; and ≤10.0 ppm Ni, based on the total iron oxide containing effect pigment as determined by total dissolution.

20. The iron oxide containing effect pigment of claim 1, wherein the iron oxide containing effect pigment further comprises ≤12.0 ppm Ba; ≤1.0 ppm Pb; and ≤8.0 ppm Ni, based on the total iron oxide containing effect pigment as determined by total dissolution.

21. The method of claim 6, wherein the iron oxide containing effect pigment further comprises ≤30.0 ppm Ba;

≤10.0 ppm Pb; and ≤10.0 ppm Ni, based on the total iron oxide containing effect pigment as determined by total dissolution.

22. The method of claim 6, wherein the iron oxide containing effect pigment further comprises ≤12.0 ppm Ba; ≤1.0 ppm Pb; and ≤8.0 ppm Ni, based on the total iron oxide containing effect pigment as determined by total dissolution.

23. The method of claim 6, wherein the substrate comprises synthetic mica.

* * * * *